United States Patent
Ogura et al.

(12) 
(10) Patent No.: US 6,440,079 B1
(45) Date of Patent: Aug. 27, 2002

(54) SUPERIOR-AND-INFERIOR-LIMB BLOOD-PRESSURE INDEX MEASURING APPARATUS

(75) Inventors: Toshihiko Ogura; Takashi Honda; Hideichi Tsuda, all of Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/977,343

(22) Filed: Oct. 16, 2001

(30) Foreign Application Priority Data

Nov. 6, 2000 (JP) ........................................ 2000-338060

(51) Int. Cl.$^7$ ................................................ A61B 5/06
(52) U.S. Cl. ........................ 600/492; 600/500; 600/485; 600/494
(58) Field of Search ............................ 600/492–6, 485, 600/500

(56) References Cited

U.S. PATENT DOCUMENTS 6,355,000 B1 * 3/2002 Ogura ........................ 600/490
6,379,309 B1 * 4/2002 Ogura et al. ................ 600/490

* cited by examiner

Primary Examiner—Robert Nassar
(74) Attorney, Agent, or Firm—Oliff & Berridge, PLC

(57) ABSTRACT

An apparatus for measuring a superior-and-inferior-limb blood-pressure index of a living subject, including a first measuring device which measures a first blood pressure of an inferior limb; a second measuring device which measures a second blood pressure of a superior limb; an information obtaining device for iteratively obtaining information changing in relation with change of blood pressure of the subject; a change-value determining device for determining a change value of blood pressure of the subject between a first time when the first blood pressure is measured and a second time when the second blood pressure is measured, based on a first piece of information obtained by the information obtaining device at the first time and a second piece of information obtained by the information obtaining device at the second time; a corrected-blood-pressure determining device for determining, based on the determined change value, one of the first and second blood pressures to a corrected blood pressure that would have been measured at one of the first and second times that corresponds to the other of the first and second blood pressures; and an index determining device for determining the superior-and-inferior-limb blood-pressure index, based on the determined corrected blood pressure and the other of the first and second blood pressures that has not been corrected by the corrected-blood-pressure determining device.

8 Claims, 6 Drawing Sheets

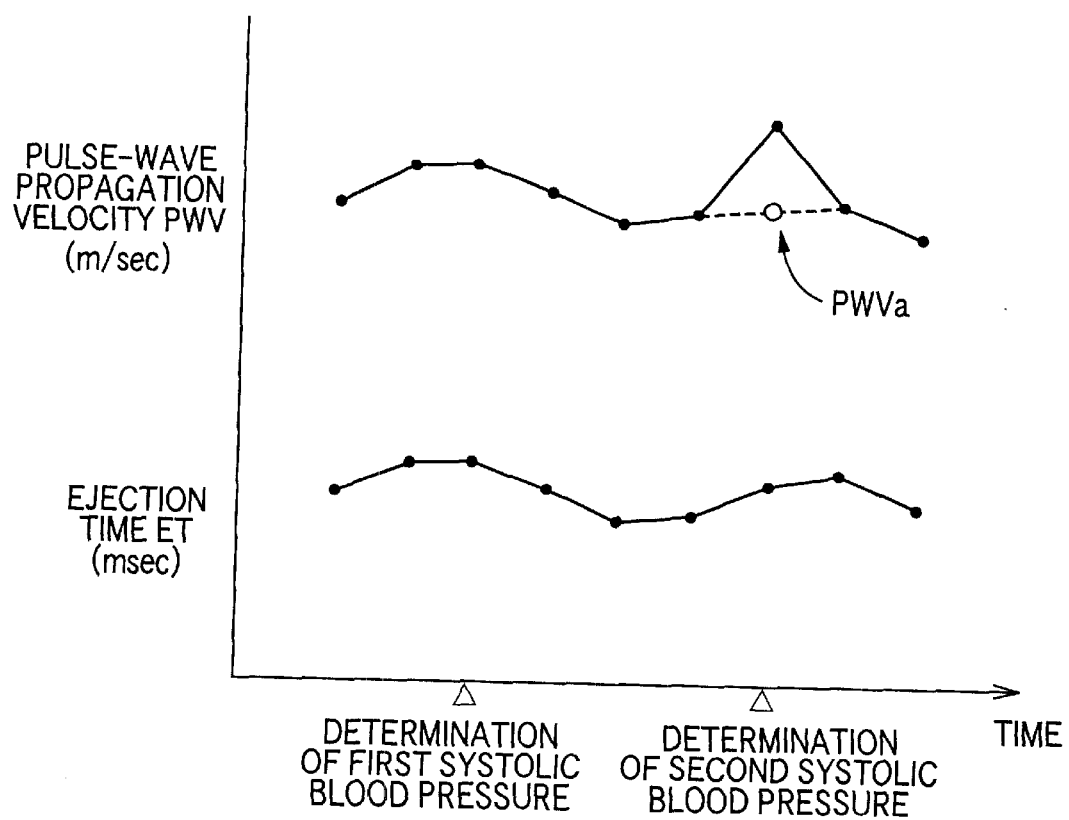

SUPERIOR-AND-INFERIOR-LIMB BLOOD-PRESSURE INDEX MEASURING APPARATUS

BACKGROUND OF THE INVENTION

1. Field of the Invention

The present invention relates to an apparatus for measuring a superior-and-inferior-limb blood-pressure index of a living subject (e.g., a ratio of an inferior-limb blood pressure to a superior-limb blood pressure, or a ratio of a superior-limb blood pressure to an inferior-limb blood pressure).

2. Related Art Statement

Arteriosclerotic cardiovascular disease is one of major death causes of aged women, e.g., not younger than sixty-five-year old, but there is no easy method of finding latent arteriosclerosis. However, it is known that since measurement of superior-and-inferior-limb blood-pressure index can be used as a simple and repeatable method to find inferior-limb arterial disease and can be used to check quickly and easily the condition of whole cardiovascular system, the index is useful to identify individuals who need special treatments to reduce their death rate or incidence rate.

Generally, the above-mentioned superior-and-inferior-limb blood-pressure ("BP") index is obtained as the ratio of a systolic blood pressure of an ankle as the inferior-limb to a systolic blood pressure of an upper arm as the superior-limb, that is, ankle/upper-arm BP index (abbreviated to "ABI"). If the measured ankle/upper-arm BP index of a living subject is smaller than a prescribed value, e.g., about 0.9, abnormality may be diagnosed on the subject. Thus, a small change of the systolic blood pressure of the inferior limb such as ankle or a small change of the systolic blood pressure of the superior limb such as upper arm largely influences the diagnosis made on the subject. On the other hand, since blood pressure of each living subject may change in a short time, a conventional super-and-inferior-limb BP index measuring apparatus simultaneously starts increasing respective pressures of two cuffs respectively wound around the superior and inferior limbs to measure respective systolic BP values of the superior and inferior limbs.

However, even if the respective increasing of respective pressures of the two cuffs may be simultaneously started, there exist a certain amount of difference between the respective systolic BP values of the superior and inferior limbs. Therefore, there exists a certain time difference between respective times when the respective systolic BP values of the superior and inferior limbs are determined. The time difference corresponds to a few heartbeats of the subject. Meanwhile, the blood pressure of the subject contains a respiratory change corresponding to his or her respiration period. Thus, the blood pressure of the subject may change between the respective times of determination of the respective systolic BP values of the superior and inferior limbs. Thus, the superior-and-inferior-limb BP index determined by the conventional apparatus cannot enjoy a sufficiently high accuracy.

SUMMARY OF THE INVENTION

It is therefore an object of the present invention to provide a superior-and-inferior-limb blood-pressure index measuring apparatus which can measure a highly accurate superior-and-inferior blood-pressure index.

The Inventors have carried out extensive studies and found that if blood-pressure-relating information changing with blood pressure is iteratively obtained when inferior-limb and superior-limb blood pressures (systolic, mean, or diastolic blood pressures) are measured, a change of the blood pressure between respective times of measurement of the inferior-limb and superior-limb blood pressures is determined based on the iteratively obtained pieces of blood-pressure-relating information, and one of the inferior-limb and superior-limb blood pressures is corrected based on the thus determined blood-pressure change, then a highly accurate superior-and-inferior-limb blood-pressure index is obtained. The present invention has been developed based on this finding.

The above object has been achieved by the present invention. According to the present invention, there is provided an apparatus for measuring a superior-and-inferior-limb blood-pressure index of a living subject, comprising a first blood-pressure measuring device which includes at least one first inflatable cuff adapted to be wound around an inferior limb of the subject and measures a first blood pressure of the inferior limb; a second blood-pressure measuring device which includes a second inflatable cuff adapted to be wound around a superior limb of the subject and measures a second blood pressure of the superior limb; a blood-pressure-relating-information obtaining device for iteratively obtaining, from the subject, a piece of blood-pressure-relating information changing in relation with a change of a blood pressure of the subject; a blood-pressure-change-value determining means for determining a change value of the blood pressure of the subject between a first time when the first blood pressure is measured by the first blood-pressure measuring device and a second time when the second blood pressure is measured by the second blood-pressure measuring device, based on a first piece of blood-pressure-relating information obtained by the blood-pressure-relating-information obtaining device at the first time and a second piece of blood-pressure-relating information obtained by the blood-pressure-relating-information obtaining device at the second time; a corrected-blood-pressure determining means for determining, based on the change value determined by the blood-pressure-change-value determining means, one of the first and second blood pressures to a corrected blood pressure that would have been measured at one of the first and second times that corresponds to the other of the first and second blood pressures; and a blood-pressure-index determining means for determining the superior-and-inferior-limb blood-pressure index, based on the corrected blood pressure determined by the corrected-blood-pressure determining means and said other of the first and second blood pressures that has not been corrected by the corrected-blood-pressure determining means.

According to this invention, the blood-pressure-change-value determining means determines the change value of the blood pressure of the subject between the first time when the first blood pressure is measured by the first blood-pressure measuring device and the second time when the second blood pressure is measured by the second blood-pressure measuring device, based on the first piece of blood-pressure-relating information obtained by the blood-pressure-relating-information obtaining device at the first time and the second piece of blood-pressure-relating information obtained by the blood-pressure-relating-information obtaining device at the second time, and the corrected-blood-pressure determining means determines, based on the change value determined by the blood-pressure-change-value determining means, one of the first and second blood pressures to a corrected blood pressure that would have been measured at one of the first and second times that corresponds to the other of the first and second blood pressures. And, the blood-pressure-index determining means determines the superior-and-inferior-limb blood-pressure index, based on the corrected blood pressure determined by the corrected-blood-pressure determining means and the other of the first and second blood pressures that has not been corrected by the corrected-blood-pressure determining means. Since the superior-and-inferior-limb blood-pressure index is determined based on the two blood-pressure values measured at the same time, it enjoys a high accuracy.

Preferably, the blood-pressure-relating-information obtaining device comprises a pulse-wave-propagation-velocity-relating-information obtaining device which iteratively obtains, as the piece of blood-pressure-relating information, a piece of pulse-wave-propagation-velocity-relating information relating to a velocity at which a pulse wave propagates through an artery of the subject.

Since the pulse-wave-propagation-velocity-relating information is one of those sorts of blood-pressure-relating information that change most faithfully corresponding to the change of blood pressure, each of the change value determined by the blood-pressure-change-value determining means, the corrected blood pressure obtained based on the change value, and the superior-and-inferior-limb blood-pressure index determined based on the corrected blood pressure enjoys a high accuracy.

Preferably, the first blood-pressure measuring device includes a right-ankle first inflatable cuff adapted to be wound around a right ankle of the subject, and a left-ankle first inflatable cuff adapted to be wound around a left ankle of the subject, and measures a right-ankle first blood pressure of the right ankle and a left-ankle first blood pressure of the left ankle, the blood-pressure-change-value determining means determines a right-ankle first change value of the blood pressure of the subject between a right-ankle first time when the right-ankle first blood pressure is measured by the first blood-pressure measuring device and the second time when the second blood pressure is measured by the second blood-pressure measuring device, based on a right-ankle first piece of blood-pressure-relating information obtained by the blood-pressure-relating-information obtaining device at the right-ankle first time and the second piece of blood-pressure-relating information obtained by the blood-pressure-relating-information obtaining device at the second time, and additionally determines a left-ankle first change value of the blood pressure of the subject between a left-ankle first time when the left-ankle first blood pressure is measured by the first blood-pressure measuring device and the second time, based on a left-ankle first piece of blood-pressure-relating information obtained by the blood-pressure-relating information obtaining device at the left-ankle first time and the second piece of blood-pressure-relating information obtained by the blood-pressure-relating-information obtaining device at the second time, the corrected-blood-pressure determining means corrects, based on the right-ankle change value determined by the blood-pressure-change-value determining means, one of the right-ankle first blood pressure and the second blood pressure to a corrected blood pressure that would have been measured at one of the right-ankle first time and the second time that corresponds to the other of the right-ankle first blood pressure and the second blood pressure, and additionally corrects, based on the left-ankle change value determined by the blood-pressure-change-value determining means, one of the left-ankle first blood pressure and the second blood pressure to a corrected blood pressure that would have been measured at one of the left-ankle first time and the second time that corresponds to the other of the left-ankle first blood pressure and the second blood pressure, and the blood-pressure-index determining means determines a right-side blood-pressure index, based on the corrected blood pressure determined by the corrected-blood-pressure determining means and the other of the right-ankle first blood pressure and the second blood pressure that has not been corrected by the corrected-blood-pressure determining means, and additionally determines a left-side blood-pressure index, based on the corrected blood pressure determined by the corrected-blood-pressure determining means and said other of the left-ankle first blood pressure and the second blood pressure that has not been corrected by the corrected-blood-pressure determining means.

According to this feature, the blood-pressure-index determining means determines both the right-side blood-pressure index and the left-side blood-pressure index. Since the lower one of the two blood-pressure index values can be used to make a diagnosis on the subject, the diagnosis enjoys a higher accuracy. In some cases, a blood pressure of an ankle may not be accurately measured because a tibia or a fibula prevents a posterior tibial artery from being sufficiently pressed, that is, a higher blood pressure than an accurate blood pressure may be measured. In those cases, an accurate diagnosis may not be expected. However, according to this feature, at least one of the right-side blood-pressure index and the left-side blood-pressure index is expected to be accurate. Thus, a more accurate diagnosis may be made based on the lower one of the two blood-pressure index values.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 6 is a graph showing respective examples of pulse-wave-propagation velocities, and ejection times, that are iteratively determined in the embodiment shown in FIG. 5.

DETAILED DESCRIPTION OF PREFERRED EMBODIMENTS

Figure 1:
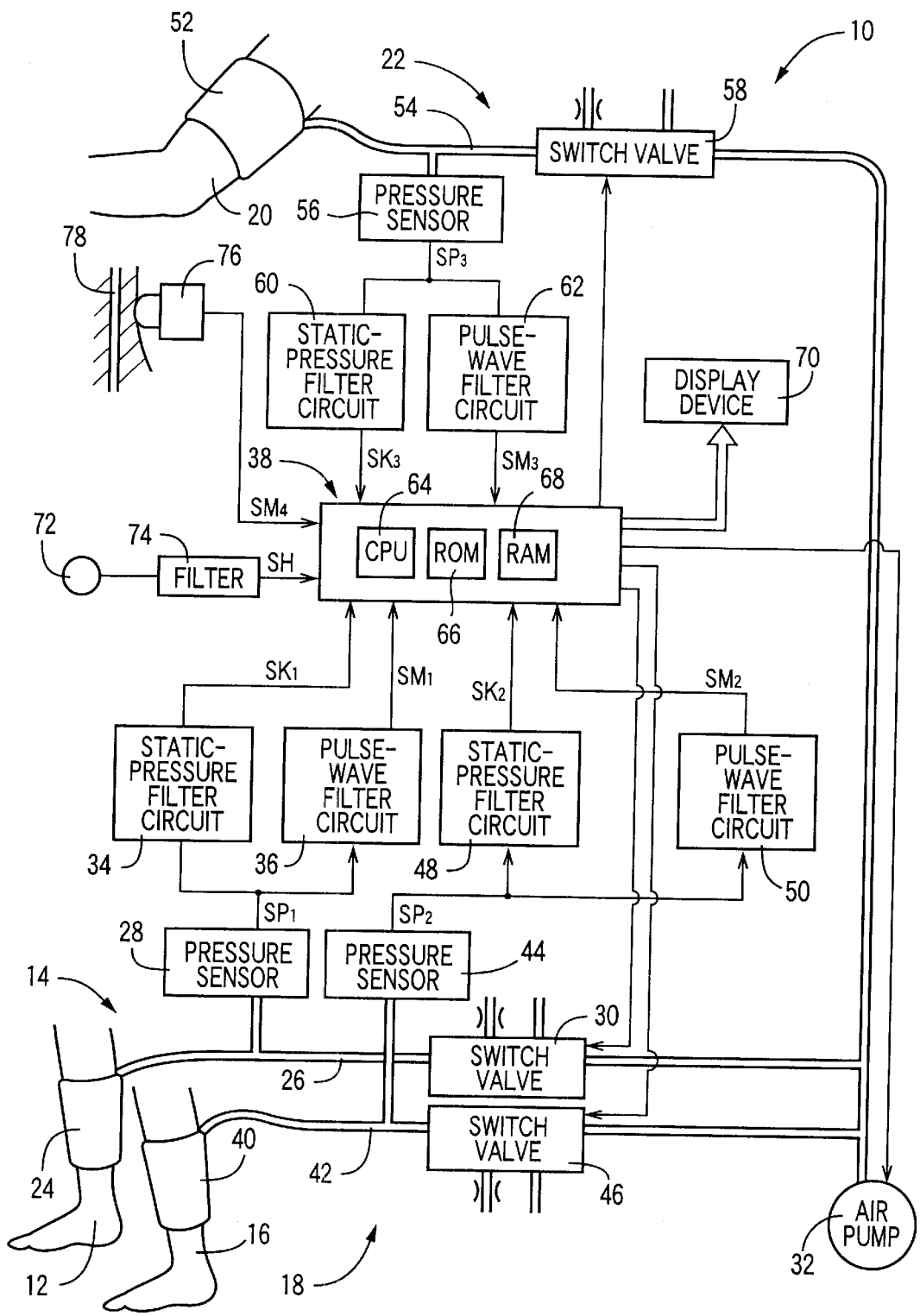
FIG. 1 is a diagrammatic view of a construction of an ankle/upper-arm blood-pressure index measuring apparatus to which the present invention is applied.

Hereinafter, there will be described an embodiment of the present invention in detail by reference to the drawings. FIG. 1 shows a diagrammatic view for explaining a construction of an ankle/upper-arm blood-pressure ("BP") index measuring apparatus 10 to which the present invention is applied.

The ankle/upper-arm BP index measuring apparatus 10 is a sort of superior-and-inferior-limb BP index measuring apparatus, since the apparatus 10 measures, as an inferior-limb BP value, a BP value from an ankle of a patient as a living person and measures, as a superior-limb BP value, a BP value from an upper arm of the patient. The present apparatus 10 carries out measurements on the patient who takes a face-down, lateral, or face-up position so that the upper arm and the ankle are substantially level with each other.

In FIG. 1, the ankle/upper-arm BP index measuring apparatus 10 includes a right-leg first BP measuring device 14 which measures a BP value from a right ankle 12 of the patient, a left-leg first BP measuring device 18 which measures a BP value from a left ankle 16 of the patient, and a second BP measuring device 22 which measures a BP value from an upper arm 20 of the patient.

The right-leg first BP measuring device 14 includes an inflatable cuff 24 which includes a belt-like cloth bag and a rubber bag accommodated in the cloth bag and which is wound around the right ankle 12 of the patient; a piping 26; and a pressure sensor 28, a switch valve 30, and an air pump 32 which are connected to the cuff 24 via the piping 26. The switch valve 30 is selectively placed in one of three positions, that is, (a) a pressure-supply position in which the switch valve 30 allows pressurized air to be supplied from the air pump 32 to the cuff 24, (b) a slow-deflation position in which the valve 30 allows the pressurized air to be slowly discharged from the cuff 24, and (c) a quick-deflation position in which the valve 30 allows the pressurized air to be quickly discharged from the cuff 24.

The pressure sensor 28 detects an air pressure in the Cuff 24, and supplies a pressure signal, $SP_1$, representing the detected air pressure, to a static-pressure filter circuit 34 and a pulse-wave filter circuit 36. The static-pressure filter circuit 34 includes a low-pass filter which extracts, from the pressure signal $SP_1$, a cuff-pressure signal, $SK_1$, representing a cuff pressure, $P_{C1}$, as a static component of the detected air pressure. The filter circuit 34 supplies the cuff-pressure signal $SK_1$, to a control device 38 via an analog-to-digital ("A/D") converter, not shown.

The pulse-wave filter circuit 36 includes a band-pass filter which extracts, from the pressure signal $SP_1$, a pulse-wave signal, $SM_1$, representing a pulse wave as an oscillatory component of the detected air pressure that has prescribed frequencies. The filter circuit 36 supplies the pulse-wave signal $SM_1$ to the control device 38 via an A/D converter, not shown.

The left-leg first BP measuring device 18 includes an inflatable cuff 40, a piping 42, a pressure sensor 44, and a switch valve 46 which have respective constructions identical with those of the counterparts 24, 26, 28, 30 of the right-leg first BP measuring device 14. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-leg first BP measuring device 14. The static-pressure filter circuit 48 extracts, from the pressure signal $SP_2$, a cuff-pressure signal, $SK_2$, representing a cuff pressure, $P_{C2}$, as a static component of the detected air pressure, and supplies the cuff-pressure signal $SK_2$ to the control device 38 via an A/D converter, not shown. The pulse-wave filter circuit 50 extracts, from the pressure signal $SP_2$, a pulse-wave signal, $SM_2$, representing a pulse wave as an oscillatory component of the detected air pressure that has prescribed frequencies, and supplies the pulse-wave signal $SM_2$ to the control device 38 via an A/D converter, not shown.

The second BP measuring device 22 includes an inflatable cuff 52 which has a construction identical with the cuff 24 or 40 and which is wound around an upper arm 20 (e.g., a right upper arm) of the patient; and a piping 54, a pressure sensor 56, and a switch valve 58 which have respective constructions identical with those of the counterparts 26, 28, 30 of the right-leg first BP measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the -counterparts 34, 36 of the right-leg first BP measuring device 14. The static-pressure filter circuit 60 extracts, from the pressure signal $SP_3$, a cuff-pressure signal, $SK_3$, representing a cuff pressure, $P_{C3}$, as a static component of the detected air pressure, and supplies the cuff-pressure signal $SK_3$ to the control device 38 via an A/D converter, not shown. The pulse-wave filter circuit 62 extracts, from the pressure signal $SP_3$, a pulse-wave signal, $SM_3$, representing a pulse wave as an oscillatory component of the detected air pressure that has prescribed frequencies, and supplies the pulse-wave signal $SM_3$ to the control device 38 via an A/D converter, not shown.

The control device 38 is essentially provided by a microcomputer including a central processing unit ("CPU") 64, a read only memory ("ROM") 66, a random access memory ("RAM") 68, and an input-and-output ("I/O") port, not shown, and processes input signals according to the control programs pre-stored in the ROM 66, while utilizing the temporary-storage function of the RAM 68. The control device 38 outputs, from the I/O port, drive signals to the air pump 32 and the three switch valves 30, 46, 58 to control the respective operations thereof, and additionally outputs display signals to a display device 70 to control the contents displayed thereby.

A microphone 72 is attached, with an adhesive tape, not shown, to the skin of central portion of the chest of the patient, more specifically described, a prescribed heart-sound-detect position right above the apex cordis, the left end of the fourth intercostal sternum, the left end of the second intercostal sternum, the right end of the second intercostal sternum, or the right end of the fourth intercostal sternum. The microphone 72 detects heart sounds which are transmitted from the heart to the skin of the prescribed heart-sound-detect position. The heart sounds are produced when the heart starts outputting blood to the aorta, and when the heart ends outputting blood to the aorta. Thus, the heart sounds provide a pulse wave which is produced from the most upstream portion of the aorta. The microphone 72 functions as a first pulse-wave detecting device.

Figure 2:
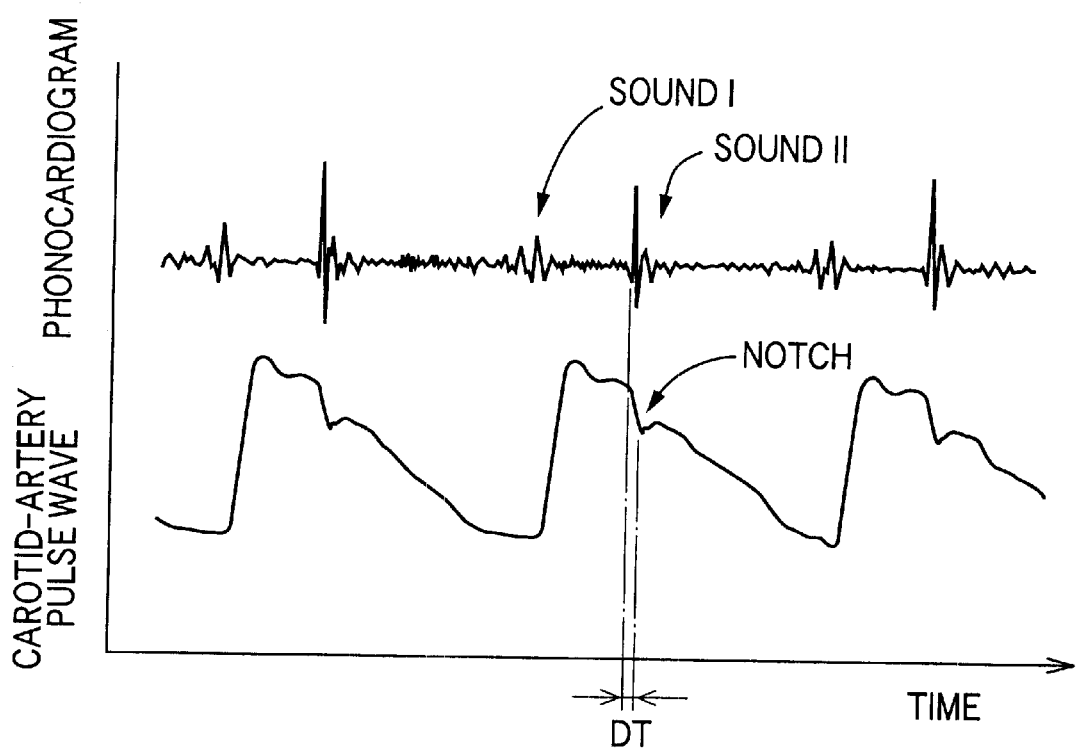
FIG. 2 is a graph showing respective examples of a phonocardiogram detected by a microphone of the apparatus of FIG. 1, and a carotid-artery pulse wave detected by a carotid-artery pulse-wave sensor of the same apparatus.

The microphone 72 includes a piezoelectric element, not shown, which converts the sounds detected thereby into an electric signal, i.e., a heart-sound signal, SH, and outputs the heart-sound signal SH, which subsequently is amplified by a preamplifier, not shown, and is supplied to a filter device 74. Then, the signal SH is supplied to the control device 38 via a main amplifier and an A/D converter, both not shown. The filter device 74 includes four sorts of filters, not shown, which can be so selected and used that the low-pitched-sound components of the heart-sound signal SH are attenuated and the high-pitched-sound components thereof are exaggerated and accordingly the heart sounds can be heard by the auditory sense of a human being. An upper half portion of FIG. 2 shows an example of phonocardiogram detected by the microphone 72. The phonocardiogram includes a first sound I corresponding to the closing of the mitral valve and the opening of the aortic valve, and a second sound II corresponding to the closing of the aortic valve.

A carotid-artery pulse-wave sensor 76 functions as a second pulse-wave detecting device which is worn on a portion of the patient that is located on a downstream side of the microphone 72 as the first pulse-wave detecting device, as seen in the direction of flowing of blood in the body of the patient, and which detects a pulse wave propagating through an artery running in that portion of the patient. The pulse-wave sensor 76 includes a contact member, and a vibration sensor, not shown, which detects vibration of the contact member. The pulse-wave sensor 76 is attached to the neck of the patient such that the contact member is held in pressed contact with the skin right above a carotid artery 78 and detects a carotid-artery pulse wave produced from the carotid artery 78. The pulse-wave sensor 76 supplies a signal, $SM_4$, representing the detected carotid-artery pulse wave, to the control device 38 via an A/D converter, not shown. A lower half portion of FIG. 2 shows an example of the carotid-artery pulse wave detected by the pulse-wave sensor 76. Since the carotid artery 78 has a considerably great diameter and is directly connected to the aorta, the waveform of the carotid-artery pulse wave is substantially identical with that of aortic pulse wave.

Figure 3:
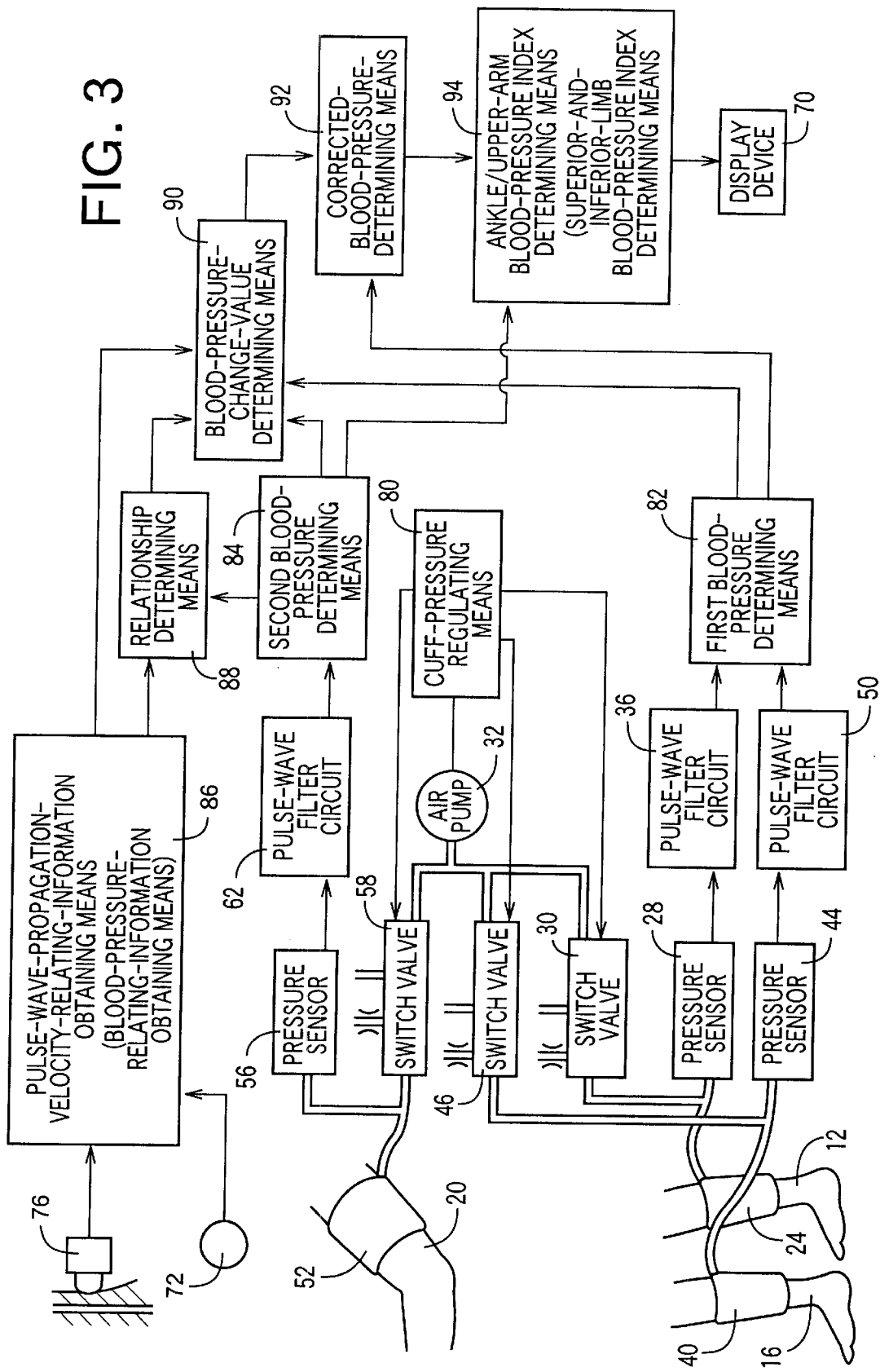
FIG. 3 is a diagrammatic view for explaining essential functions of a control device of the apparatus of FIG. 1.

FIG. 3 is a diagrammatic view for explaining essential control functions of the control device 38. A cuff-pressure regulating means 80 controls the air pump 32 and the three switch valves 30, 46, 58, such that the respective pressing pressures of the three cuffs 24, 40, 52 are quickly increased up to a predetermined target pressure value, $P_{CM}$, (e.g., about 180 mmHg) and then are slowly decreased at a rate of about 3 mmHg/sec.

A first BP determining means 82 determines right-leg first BP values, $BP1_R$, that is, BP values of the right ankle 12, according to well-known oscillometric method, based on the change of respective amplitudes of the heartbeat-synchronous pulses of the pulse-wave signal $SM_1$ detected one by one during the slow deflation of the cuff 24 wound around the right ankle 12 under the control of the cuff-pressure regulating means 80. In addition, the first BP determining means 82 determines left-leg first BP values, $BP1_L$, that is, BP values of the left ankle 16, according to the oscillometric method, based on the change of respective amplitudes of the heartbeat-synchronous pulses of the pulse-wave signal $SM_2$ detected one by one during the slow deflation of the cuff 40 wound around the left ankle 16 under the control of the cuff-pressure regulating means 80. The right-leg first BP values $BP1_R$ include a systolic BP value $BP1_{RSYS}$ and a diastolic BP value $BP1_{RDIA}$, and the left-leg first BP values $BP1_L$ include a systolic BP value $BP1_{LSYS}$ and a diastolic BP value $BP1_{LDIA}$. Hereinafter, when it is not needed to distinguish the right-leg first BP values $BP1_R$ and the left-leg first BP values $BP1_L$ from each other, those BP values will be wholly referred to as the first BP values BP1.

A second BP determining means 88 determines second BP values, BP2, (systolic BP value $BP2_{SYS}$ and diastolic BP value $BP2_{DIA}$), that is, BP values of the upper arm 20, according to the well-known oscillometric method, based on the change of respective amplitudes of the heartbeat-synchronous pulses of the pulse-wave signal $SM_3$ detected one by one during the slow deflation of the cuff 52 wound around the upper arm 20 under the control of the cuff-pressure regulating means 80.

A pulse-wave-propagation-velocity-relating-information obtaining means 86 iteratively obtains a piece of pulse-wave-propagation-velocity-relating-information, such as a time difference between a periodic point on each of the heartbeat-synchronous pulses of the first pulse wave detected by the microphone 72 as the first pulse-wave detecting device, and a periodic point on a corresponding one of the heartbeat-synchronous pulses of the second pulse wave detected by the sensor 76 as the second pulse-wave detecting device. For example, the information obtaining means 86 includes a time-difference determining means which iteratively determines a time difference (i.e., a pulse-wave propagation time), DT, shown in FIG. 2, that is, a time difference between a time point at which the microphone 72 detects the commencement of second heart sound II (this point corresponds to a notch of the aortic pulse wave where the amplitude ends quick decreasing and then starts increasing), and a time point at which the sensor 76 detects the notch of the carotid-artery pulse wave. The information obtaining means 86 iteratively determines, based on the time difference DT iteratively determined by the time-difference determining means for each of the heartbeat-synchronous pulses, a velocity PWV (m/sec) at which the pulse wave propagates through the artery of the patient, according to the following expression (1) pre-stored in the ROM 66:

$$PWV = L/DT \qquad (1)$$

where L(m) is the distance from the left ventricle of the heart, via the aorta, to the position where the sensor 76 is worn, and is replaced with a constant value which is experimentally obtained in advance.

Each of the pulse-wave propagation time DT and the pulse-wave propagation velocity PWV changes in relation with the blood pressure of the living subject, and accordingly is a sort of blood-pressure-relating information. Thus, the pulse-wave-propagation-velocity-relating-information obtaining means 86 is a sort of blood-pressure-relating-information obtaining means.

A relationship determining means 88 determines a relationship between blood pressure and blood-pressure-relating information, based on the systolic blood pressure values $BP_{SYS}$ determined by one of the first and second BP determining means 82, 84 and the pieces of blood-pressure-relating information obtained by the blood-pressure-relating-information obtaining means. For example, either the pulse-wave propagation time values DT or the pulse-wave propagation velocity values PWV that are obtained during, or immediately before or after, the BP measuring operation in which the systolic blood pressure values $BP_{SYS}$ are determined by one of the first and second BP determining means 82, 84, are employed as the pieces of blood-pressure-relating information, and respective coefficients α and β of either one of two relationships each between estimated blood pressure EBP and time DT or velocity PWV that are represented by the following two expressions (2) and (3), respectively, are determined, in advance, based on the employed time values DT or velocity values PWV:

$$EBP = \alpha(DT) + \beta \qquad (2)$$

where α is a negative constant and β is a positive constant.

$$EBP = \alpha(PWV) + \beta \qquad (3)$$

where α is a positive constant and β is a positive constant.
For example, the coefficients α and β of the above expression (2) are determined based on a pair of a second systolic blood pressure $BP_{SYS}$ determined by the second BP determining means 84 and a pulse-wave propagation time DT determined based on a pulse of the pulse wave detected at the time of determination of the pressure $BP_{SYS}$, and another pair of another second systolic blood pressure $BP_{SYS}$ determined by the means 84 and another pulse-wave propagation time DT determined based on another pulse of the pulse wave detected at the time of determination of the latter pressure $BP_{SYS}$.

A blood-pressure-change-value determining means 90 determines a change value $\Delta BP$ of blood pressure of the patient between respective times of determination of the first and second BP values BP1, BP2, from an estimated BP value EBP determined according to the relationship determined by the relationship determining means 88 based on a piece of pulse-wave-propagation-velocity-relating information obtained by the information obtaining means 86 at the time of determination of the first BP value BP1 (i.e., one of the first systolic BP value $BP1_{SYS}$, the first mean BP value $BP1_{MEAN}$, and the first diastolic BP value $BP1_{DIA}$) by the first BP determining means 82, and another estimated BP value EBP determined according to the relationship based on another piece of pulse-wave-propagation-velocity-relating information obtained by the information obtaining means 86 at the time of determination of the second BP value BP2 (i.e., a corresponding one of the second systolic BP value $BP2_{SYS}$, the second mean BP value $BP2_{MEAN}$, and the second diastolic BP value $BP2_{DIA}$) by the second BP determining means 84. For example, supposing that EBP(1) is an estimated BP value EBP determined according to the above-indicated expression (2) or (3) based on a pulse-wave propagation time DT or a pulse-wave propagation velocity PWV obtained at the time of determination of the first systolic BP value $BP1_{SYS}$, and EBP(2) is another estimated BP value EBP determined according to the expression (2) or (3) based on another pulse-wave propagation time DT or another pulse-wave propagation velocity PWV obtained at the time of determination of the second systolic BP value $BP2_{SYS}$, the blood-pressure change value $\Delta BP$ can be defined by the following expression (4) or (5):

$$\Delta BP_{1-2} = EBP(1) - EBP(2) \quad (4)$$

$$\Delta BP_{2-1} = EBP(2) - EBP(1) \quad (5)$$

The blood-pressure change value $\alpha BP$ means an amount of change of blood pressure of the patient after one of the first and second BP values BP1, BP2 is measured and before the other of the first and second BP values BP1, BP2 is measured.

A corrected-blood-pressure determining means 92 corrects, based on the blood-pressure change value $\Delta BP$ determined by the blood-pressure-change-value determining means 90, one of the first and second BP values BP1, BP2 to a corrected BP value CBP that would have been determined at the time of determination of the other of the first and second BP values BP1, BP2. For example, the change value $\Delta BP$ determined according to the expression (5) is added to the first systolic BP value $BP_{SYS}$, to determine a corrected systolic BP value $CBP_{SYS}$. The corrected systolic BP value $CBP_{SYS}$ means a systolic BP value of the ankle at the time of determination of the second systolic BP value $BP2_{SYS}$.

An ankle/upper-arm BP index determining means 96, functioning as the superior-and-inferior-limb BP index determining means, determines an ankle/upper-arm BP index value (hereinafter, referred as the "ABI value") based on the corrected blood pressure CBP determined by the corrected-blood-pressure determining means 92 and the non-corrected, other of the first and second BP values BP1, BP2. An index ABI is obtained by dividing an ankle blood pressure by an upper-arm blood pressure, or dividing an upper-arm blood pressure by an ankle blood pressure. Therefore, in the case where the corrected-blood-pressure determining means 92 corrects the first BP value BP1 to a corrected BP value CBP, the index ABI is obtained by dividing the corrected BP value CBP by the second BP value BP2, or dividing the second BP value BP2 by the corrected BP value CBP; and in the case where the corrected-blood-pressure determining means 92 corrects the second BP value BP2 to a corrected BP value CBP, the index ABI is obtained by dividing the first BP value BP1 by the corrected BP value CBP, or dividing the corrected BP value CBP by the first BP value BP1.

Figure 4:
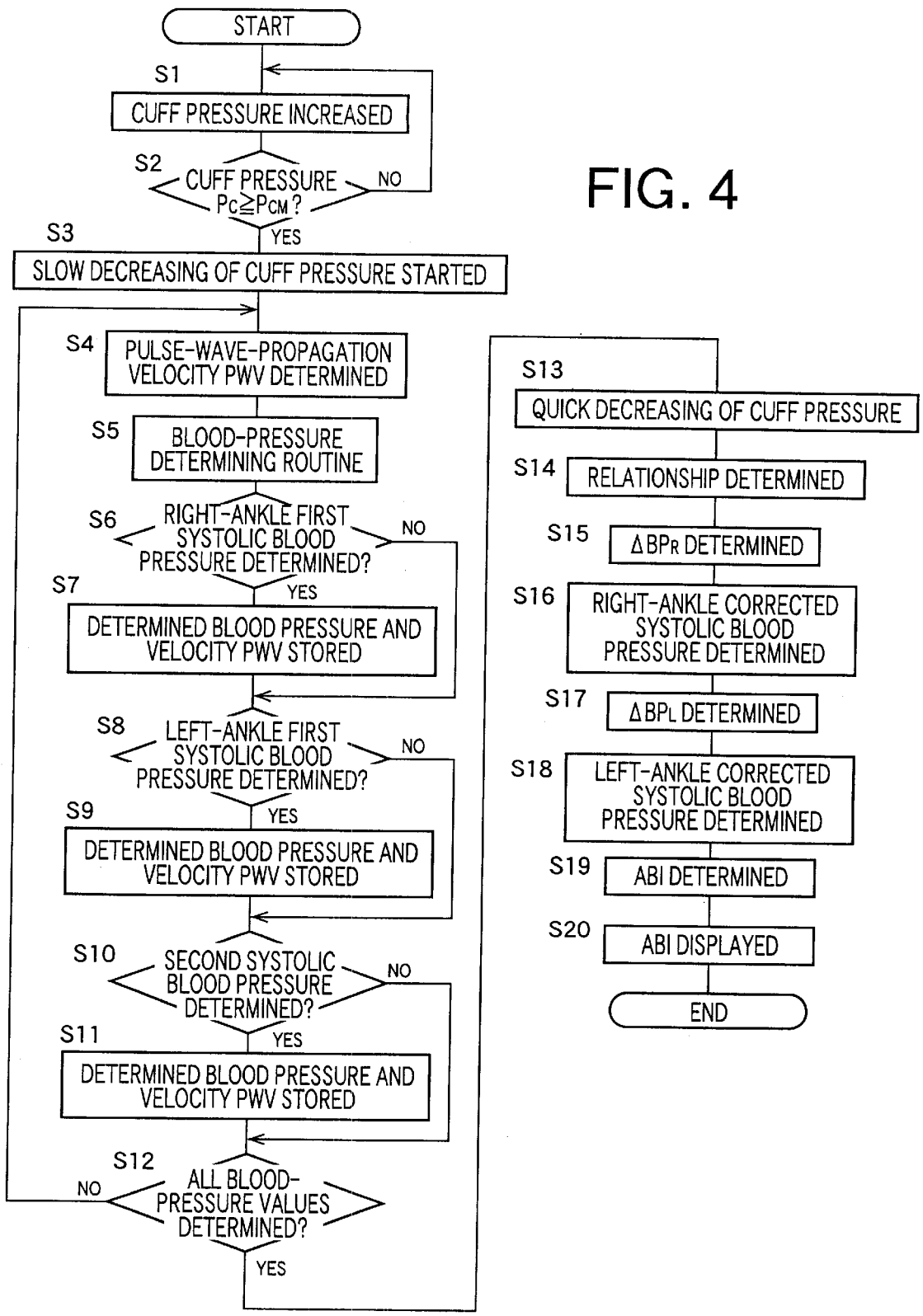
FIG. 4 is a flow chart representing a control program according to which the control device of the apparatus of FIG. 1 is operated.

FIG. 4 is a flow chart representing a control program according to which the control device 38 is operated. In the flow chart of FIG. 4, first, the control device 38 carries out Steps S1, S2, and S3 (hereinafter, "Step(s)" is omitted, if appropriate) corresponding to the cuff-pressure regulating means 80. At S1, the three switch valves 30, 46, 58 are switched to their pressure-supply positions and the air pump 32 is operated, so that the respective air pressures of the three cuffs 24, 40, 52 are quickly increased. At S2, it is judged whether all the air pressures $P_C$ of the three cuffs 24, 40, 52 have reached the predetermined target pressure value $P_{CM}$ (about 180 mmHg). If a negative judgment is made at S2, Steps S1 and S2 are repeated to continue increasing the air pressures $P_C$ of the cuffs 24, 40, 52.

If a positive judgment is made at S2, the control goes to S3 to stop the operation of the air pump 32 and switch the three switch valves 30, 46, 58 to their slow-deflation positions, so that the respective air pressures $P_C$ of the three cuffs 24, 40, 52 are decreased slowly at a predetermined low rate of about 3 mmHg/sec.

Then, at S4 corresponding to the pulse-wave-propagation-velocity-relating-information obtaining means 86, the control device 38 determines, as illustrated in FIG. 2, a time difference between a time when the microphone 72 detects the commencement of second heart sound II and a time when the carotid-artery pulse-wave sensor 76 detects the notch of carotid-artery pulse wave, i.e., a pulse-wave propagation time DT that is a time needed for a pulse wave to propagate from the heart to the position where the sensor 76 is worn. The control device 38 determines a pulse-wave propagation velocity PWV based on the thus determined pulse-wave propagation time DT according to the above-indicated expression (1): PWV=L/DT.

Then, the control goes to S5, the BP-determining routine corresponding to the first BP determining means 82 and the second BP determining means 84. More specifically described, the control device 38 determines an amplitude of each of successive heartbeat-synchronous pulses of the cuff pulse wave represented by the pulse-wave signal $SM_1$ continuously supplied from the pulse-wave filter circuit 36, and determines a right-ankle first systolic BP value $BP1_{RSYS}$ based on the time-wise change of the thus determined amplitudes according to well-known oscillometric BP-determining algorithm. Similarly, the control device 38 determines an amplitude of each of successive heartbeat-synchronous pulses of the cuff pulse wave represented by the pulse-wave signal $SM_2$ continuously supplied from the pulse-wave filter circuit 50, and determines a left-ankle first systolic BP value $BP1_{LSYS}$ based on the time-wise change of the thus determined amplitudes according to the oscillometric BP-determining algorithm. In addition, the control device 38 determines an amplitude of each of successive heartbeat-synchronous pulses of the cuff pulse wave represented by the pulse-wave signal $SM_3$ continuously supplied from the pulse-wave filter circuit 62, and determines a second systolic BP value $BP2_{SYS}$, based on the time-wise change of the thus determined amplitudes according to the oscillometric BP-determining algorithm.

At Steps S6 to S11, the control device 38 judges whether each of the above-indicated three systolic BP values (i.e., three maximal BP values) $BP1_{RSYS}$, $BP1_{LSYS}$, $BP2_{SYS}$ of the patient has been determined. When each one of the three systolic BP values is determined, the each one systolic BP value is stored, in the RAM 68, together with a pulse-wave-propagation velocity PWV obtained at the time of determination of the each one systolic BP value.

More specifically described, at S6, the control device 38 judges whether the right-ankle first systolic BP value $BP1_{RSYS}$ of the patient has been determined. If a negative judgment is made at S6, the control directly goes to S8 but, if a positive judgment is made at S6, the control goes to S7 to store, in a prescribed memory area of the RAM 68, the determined right-ankle first systolic BP value $BP1_{RSYS}$ and the pulse-wave-propagation velocity PWV determined at S4 immediately before the positive judgment is made at S6. At S8, the control device 38 judges whether the left-ankle first systolic BP value $BP1_{LSYS}$ of the patient has been determined. If a negative judgment is made at S8, the control directly goes to S10 but, if a positive judgment is made at S8, the control goes to S9 to store, in the prescribed memory area of the RAM 68, the determined left-ankle first systolic BP value $BP1_{LSYS}$ and the pulse-wave-propagation velocity PWV determined at S4 immediately before the positive judgment is made at S8. At S10, the control device 38 judges whether the second systolic BP value $BP2_{SYS}$ of the patient has been determined. If a negative judgment is made at S10, the control directly goes to S12 but, if a positive judgment is made at S10, the control goes to S11 to store, in the prescribed memory area of the RAM 68, the determined second systolic BP value $BP2_{SYS}$ and the pulse-wave-propagation velocity PWV determined at S4 immediately before the positive judgment is made at S10.

At S12, the control device 38 judges whether all the blood-pressure values have been determined, that is, whether the right-ankle first systolic blood pressure $BP1_{RSYS}$, the left-ankle first systolic BP value $BP1_{LSYS}$ and the second systolic BP value $BP2_{SYS}$ have been determined and additionally the respective diastolic blood-pressure values (i.e., respective minimal values) of the right ankle 12, the left ankle 16, and the upper arm 20 have been determined. If a negative judgment is made at S12, Step S4 and the following steps are repeated while the pulse-wave-propagation velocity values PWV are successively determined and the blood-pressure determining routine is continuously carried out.

Meanwhile, if a positive judgment is made at S12, the control goes to S13 corresponding to the cuff-pressure regulating means 80. At S13, the three switch valves 30, 46, 58 are switched to their quick-deflation positions, so that the respective pressures of the three cuffs 24, 40, 52 are quickly lowered.

Then, the control goes to S14 corresponding to the relationship determining means 88. At S14, the control device 38 determines, based on a first combination of the second systolic blood pressure $BP2_{SYS}$, i.e., the maximal blood pressure of the upper arm 20, determined by the blood-pressure determining routine at S5, and the pulse-wave-propagation velocity PWV stored therewith at S7, and a second combination of another second systolic blood pressure $BP2_{SYS}$ measured in advance from the same patient and another pulse-wave-propagation velocity PWV measured in advance from the same patient at the time of measurement of the latter second systolic blood pressure $BP2_{SYS}$, the coefficients $\alpha$, $\beta$ of the expression (3) that is used to determine an estimated blood pressure EBP based on a pulse-wave-propagation velocity PWV.

Then, the control goes to S15 corresponding to the blood-pressure-change-value determining means 90. At S15, the control device 38 determines, according to the expression (3) the coefficients $\alpha$, $\beta$ of which have been determined at S14, an estimated blood pressure EBP(2) at the time of determination of the second systolic blood pressure $BP2_{SYS}$, based on the pulse-wave-propagation velocity PWV stored at S11, i.e., determined at the time of determination of the second systolic blood pressure $BP2_{SYS}$. Similarly, the control device 38 determines, according to the expression (3), an estimated blood pressure EBP(1R) at the time of determination of the right-ankle first systolic blood pressure $BP1_{RSYS}$, based on the pulse-wave-propagation velocity PWV stored at S7, and subtracts, according to the expression (5), the estimated blood pressure EBP(1R) from the estimated blood pressure EBP(2), to determine a change value $\Delta BP_{2-1R}$ of blood pressure of the patient from the time of determination of the right-ankle first systolic blood pressure $BP1_{RSYS}$ to the time of determination of the second systolic blood pressure $BP2_{SYS}$.

Then, the control goes to S16 corresponding to the corrected-blood-pressure determining means 92. At S16, the control device 38 adds, to the right-ankle first systolic blood pressure $BP1_{RSYS}$ stored at S7, the change value $\Delta BP_{2-1R}$ determined at S15, to determine a corrected systolic blood pressure $CBP_{SYS}$ of the right ankle 12 indicating a systolic blood pressure at the time of determination of the second systolic blood pressure $BP2_{SYS}$.

Steps S17 and S18 for the right-ankle first systolic blood pressure $BP1_{RSYS}$ are similar to Steps S15 and 16 for the left-ankle first systolic blood pressure $BP1_{LSYS}$. More specifically described, first, at S17 corresponding to the blood-pressure-change-value determining means 90, the control device 38 determines, according to the expression (3) the coefficients $\alpha$, $\beta$ of which have been determined at S14, an estimated blood pressure EBP(1L) at the time of determination of the left-ankle first systolic blood pressure $BP1_{LSYS}$, based on the pulse-wave-propagation velocity PWV stored at S9, and subtracts, according to the expression (5), the estimated blood pressure EBP(1L) from the estimated blood pressure EBP(2), to determine a change value $\Delta BP_{2-1R}$ of blood pressure of the patient from the time of determination of the left-ankle first systolic blood pressure $BP1_{LSYS}$ to the time of determination of the second systolic blood pressure $BP2_{SYS}$. Then, at S18 corresponding to the corrected-blood-pressure determining means 92, the control device 38 adds, to the left-ankle first systolic blood pressure $BP1_{LSYS}$ stored at S9, the change value $\Delta BP_{2-1R}$ determined at S17, to determine a corrected systolic blood pressure $CBP_{SYS}$ indicating a systolic blood pressure of the left ankle 12 at the time of determination of the second systolic blood pressure $BP2_{SYS}$.

Then, the control goes to S19 corresponding to the ankle/upper-arm BP index determining means 94. At S19, the control device 38 calculates a right-leg index $ABI_R$ by dividing, by the second systolic BP value $BP2_{SYS}$ stored at S11, the corrected systolic blood pressure $CPB_{SYS}$ determined at S16 by correcting the right-ankle first systolic BP value $BP1_{RSYS}$, and calculates a left-leg index $ABI_L$ by dividing, by the second systolic BP value $BP2_{SYS}$ stored at S11, the corrected systolic BP value $CBP1_{SYS}$ determined at Step S18 by correcting the left-ankle first systolic BP value $BP1_{LSYS}$.

Then, at S20, the control device 38 controls the display device 70 to display the right-leg and left-leg index values $ABI_R$, $ABI_L$ determined at Step S19.

As is apparent from the foregoing description of the illustrated embodiment, the blood-pressure-change-value determining means 90 (S15, S17) determines, based on the pulse-wave-propagation velocity PWV determined by the pulse-wave-propagation-velocity-relating-information obtaining means 86 (S4) when the first systolic blood pressure $BP1_{SYS}$ is determined by the first blood-pressure determining means 82 (S5), and the pulse-wave-propagation velocity PWV determined by the wave-propagation-velocity-relating-information obtaining means 86 (S4) when the second systolic blood pressure $BP2_{SYS}$ is determined by the second blood-pressure determining means 84 (S5), the change value ΔBP of blood pressure of the patient from the time of determination of the first systolic blood pressure $BP1_{SYS}$ to the time of determination of the second systolic blood pressure $BP2_{SYS}$; and the corrected-blood-pressure determining means 92 (S16, S18) corrects, based on the change value ΔBP determined by the blood-pressure-change-value determining means 90 (S15, S17), the first systolic blood pressure $BP1_{SYS}$ into the corrected blood pressure $CBP_{SYS}$ that would have been determined at the time of determination of the second systolic blood pressure $BP2_{SYS}$. And, the ankle/upper-arm BP index determining means 94 (S19) determines the index ABI by dividing the corrected blood pressure $CBP_{SYS}$ determined by the corrected-blood-pressure determining means 92 (S16, S18), by the second systolic blood pressure $BP2_{SYS}$ that has not been corrected by the corrected-blood-pressure determining means 92 (S16, S18). Since the index ABI is determined based on the two systolic blood-pressure values obtained at the same time, the index can enjoy a high accuracy.

Also, in the illustrated embodiment, the blood-pressure-relating-information obtaining means is provided by the pulse-wave-propagation-velocity-relating-information obtaining means 86 (S4) that successively obtains pulse-wave-propagation-velocity-relating information as one of those sorts of blood-pressure-relating information that change most faithfully corresponding to the change of blood pressure of a living subject. Therefore, each of the change value ΔBP determined by the blood-pressure-change-value determining means 90 (S15, S17), the corrected blood pressure $CBP_{SYS}$ obtained based on the change value ΔBP, and the index ABI determined based on the corrected blood pressure $CBP_{SYS}$, can enjoy a high accuracy.

In addition, in the illustrated embodiment, the ankle/upper-arm BP index determining means 94 (S19) determines the index $ABI_R$ and the index $ABI_L$. Since the lower one of the two index values can be used, a more accurate diagnosis can be made on the patient.

While the present invention has been described in its preferred embodiment by reference to the drawings, it is to be understood that the invention may otherwise be embodied.

For example, in the illustrated embodiment, the pulse-wave-propagation-velocity-relating information is used as the blood-pressure-relating information. However, heart-contraction-relating information that relates to contraction of heart, such as ejection time or period ET, pre-ejection period PEP, Q-II period, or time from closing of mitral valve to opening of aortic valve, changes in relation with change of blood pressure. Therefore, the heart-contraction-relating information may be used as the blood-pressure-relating information. Otherwise, heart rate, pulse period, or area of pulse wave that propagates through artery of living subject may be employed as the blood-pressure-relating information.

In the illustrated embodiment, each of the right-leg first BP measuring device 14, the left-leg first BP measuring device 16, and the second BP measuring device 22 employs the oscillometric blood-pressure measuring method. However, each device 14, 16, 22 may employ so-called Korotkoff-sound method in which blood-pressure values are determined based on respective values of a cuff pressure when Korotkoff sounds are first and last detected. Otherwise, each device 14, 16, 22 may employ a supersonic Doppler method in which supersonic transmitter and receiver are placed right above an artery to detect the opening and closing of the artery when the pressing force applied to the artery is changed, and thereby determine a blood pressure.

In addition, in the illustrated embodiment, both the right-ankle first systolic blood pressure $BP1_{RSYS}$ of the right ankle 12 and the left-ankle first systolic blood pressure $BP1_{LSYS}$ of the left ankle 16 are determined. However, it is possible to determine either one of the two blood-pressure values $BP1_{RSYS}$, $BP1_{LSYS}$.

In addition, in the illustrated embodiment, the microphone 72 that is worn on chest of a living subject is employed as the first pulse-wave detecting device to obtain the pulse-wave-propagation-velocity-relating information. However, it is possible to employ, as the as the first pulse-wave detecting device, an electrocardiograph that includes a plurality of electrodes adapted to be worn on a plurality of prescribed portions of a living subject, and continuously detects an electrocardiogram representing action potential of cardiac muscle of the subject through the electrodes.

In addition, in the illustrated embodiment, the respective pulse-wave-propagation velocity values PWV themselves determined by the pulse-wave-propagation-velocity-relating-information obtaining means 86 at the respective times of determination of the first systolic blood pressure $BP1_{SYS}$ and the second systolic blood pressure $BP2_{SYS}$ are used to determine the respective estimated blood-pressure values $EBP_{SYS}$. However, it is possible to improve the accuracy of pulse-wave-propagation-velocity-relating information used to determine an estimated blood-pressure EBP, in a manner described below.

Figure 5:
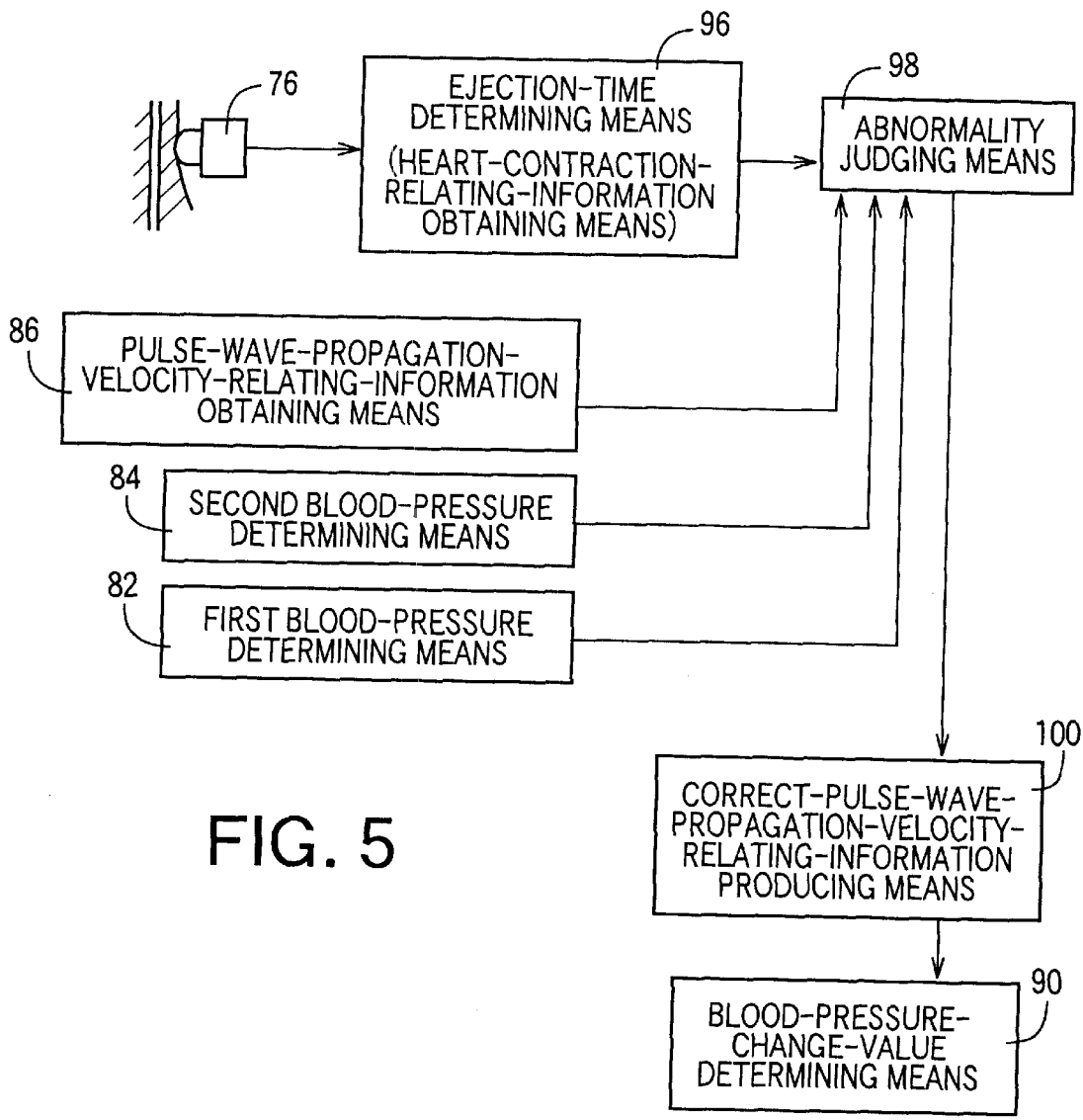
FIG. 5 is a diagrammatic view for explaining additional functions that are employed by the control device of the apparatus of FIG. 1 in another embodiment of the present invention.

FIG. 5 is a block diagram for explaining additional functions of the control device 38 that may be employed to improve the accuracy of pulse-wave-propagation-velocity-relating information. In FIG. 5, some of the other functions of the control device 38 that are not relevant to the additional functions thereof are omitted.

An ejection-time determining means 96 iteratively and non-invasively determines an ejection period or time ET in which blood is ejected from the left ventricle of the heart of a living subject. Since the ejection time ET is a sort of heart-contraction-relating information that changes in relation with change of contraction period or time of the heart of the subject, the ejection-time determining means 96 functions as heart-contraction-relating-information obtaining means. For example, the ejection-time determining means 96 determines, as the ejection time ET, a time period from a rising point (i.e., a minimal point) of one heartbeat-synchronous pulse of the carotid-artery pulse wave continuously detected by the carotid-artery pulse-wave sensor 76, to a notch of the one pulse. Since, as described above, the shape of the carotid-artery pulse wave is substantially identical with that of the aortic pulse wave, the time period from the rising point to the notch indicates a time period in which the aortic valve is open, that is, an ejection time ET.

An abnormality judging means 98 judges whether the pulse-wave-propagation-velocity-relating information obtained by the pulse-wave-propagation-velocity-relating-information obtaining means 86 at the time of determination of the first or second blood pressure BP1 or BP2, is sufficiently accurate, by comparing a tendency of change of the ejection-time values ET determined by the ejection-time determining means 96 with a tendency of change of the pieces of pulse-wave-propagation-velocity-relating information obtained by the pulse-wave-propagation-velocity-relating-information obtaining means 86. More specifically described, the judging means 98 determines a rate of change (i.e., pulse-wave-propagation-velocity-relating-information change rate) of the current piece of pulse-wave-propagation-velocity-relating information obtained by the pulse-wave-propagation-velocity-relating-information obtaining means 86 from one heartbeat-synchronous pulse of the carotid-artery pulse wave detected at the time of determination of each of the first and second blood pressure values BP1, BP2, from the preceding piece of pulse-wave-propagation-velocity-relating information obtained from the pulse preceding the one pulse, or a rate of change of the following piece of pulse-wave-propagation-velocity-relating information obtained from the pulse following the one pulse, from the current piece of pulse-wave-propagation-velocity-relating information. Similarly, the judging means 98 determines a rate of change (i.e., ejection-time change rate) of the current ejection time ET determined by the ejection-time determining means 98 from one heartbeat-synchronous pulse of the carotid-artery pulse wave detected at the time of determination of each of the first and second blood pressure values BP1, BP2, from the preceding ejection time ET determined from the pulse preceding the one pulse, or a rate of change of the following ejection time ET determined from the pulse following the one pulse, from the current ejection time ET. If the thus determined pulse-wave-propagation-velocity-relating-information change rate falls within a range that has, as its central value, the ejection-time change rate and a length that is experimentally determined in advance and is equally divided by the central value, the judging means 98 judges that the pulse-wave-propagation-velocity-relating information obtained at the time of determination of the each of the first and second blood-pressure values BP1, BP2 is sufficiently accurate.

Since both the pulse-wave-propagation-velocity-relating information and the heart-contraction-relating information, such as the ejection time ET, change in relation with the blood pressure, the pulse-wave-propagation-velocity-relating-information change rate should be substantially equal to the ejection-time change rate. That is, in FIG. 6, the tendency of change of the iteratively determined pulse-wave-propagation velocity values PWV (or the iteratively determined pulse-wave-propagation time values DT) should be substantially identical with that of the iteratively determined ejection time values ET. However, the iteratively determined pulse-wave-propagation velocity values PWV may contain measurement errors. If the pulse-wave-propagation velocity PWV determined at the time of determination of the first or second blood pressure BP1, BP2 contains a great measurement error, the blood-pressure-change-value determining means 90 would provide an inaccurate change value ΔBP, which would lead to providing an inaccurate index ABI. To solve this problem, the abnormality judging means 98 compares the tendency of change of pulse-wave-propagation-velocity-relating information and the tendency of change of heart-contraction-relating information, obtained at the time of determination of each blood pressure, with each other, and thereby judges whether the pulse-wave-propagation-velocity-relating information obtained at the time of determination of the each blood pressure is sufficiently accurate.

A correct-pulse-wave-propagation-velocity-relating-information producing means 100 produces, if the current piece of pulse-wave-propagation-velocity-relating information obtained at the time of determination of each of the first and second blood-pressure values BP1, BP2 is judged as being abnormal by the abnormality judging means 98, a correct piece of pulse-wave-propagation-velocity-relating information based on at least one preceding piece of pulse-wave-propagation-velocity-relating information obtained immediately before the current piece of information and at least one following piece of information obtained immediately after the current piece of information. For example, if, as shown in FIG. 6, the pulse-wave-propagation velocity PWV determined at the time of determination of the second systolic blood pressure $BP2_{SYS}$ is judged as being abnormal, the producing means 100 provides, as the correct pulse-wave-propagation velocity PWVa, an average of the preceding pulse-wave-propagation velocity PWV and the following pulse-wave-propagation velocity PWV. In this case, since the blood-pressure-change-value determining means 90 determines a change value ΔBP based on the thus produced correct pulse-wave-propagation velocity PWVa, the accuracy of the change value ΔBP is prevented from being lowered in spite of the large measurement error contained in the piece of pulse-wave-propagation-velocity-relating information obtained at the time of determination of the second systolic blood pressure $BP2_{SYS}$, and accordingly the accuracy of the index ABI is prevented from being lowered.

In addition, the illustrated ankle/upper-arm BP index measuring apparatus 10 is a sort of superior-and-inferior-limb BP index measuring apparatus in which an ankle is used as a portion of an inferior limb and an upper arm is used as a portion of a superior limb. However, it is possible to use, as a portion of an inferior limb, a femur or a toe or use, as a portion of a superior limb, a wrist or a finger.

It is to be understood that the present invention may be embodied with other changes, improvements and modifications that may occur to a person skilled in the art without departing from the spirit and scope of the invention defined in the appended claims.

What is claimed is:

1. An apparatus for measuring a superior-and-inferior-limb blood-pressure index of a living subject, comprising:

a first blood-pressure measuring device which includes at least one first inflatable cuff adapted to be wound around an inferior limb of the subject and measures a first blood pressure of the inferior limb;

a second blood-pressure measuring device which includes a second inflatable cuff adapted to be wound around a superior limb of the subject and measures a second blood pressure of the superior limb;

a blood-pressure-relating-information obtaining device which iteratively obtains, from the subject, a piece of blood-pressure-relating information changing in relation with a change of a blood pressure of the subject;

a blood-pressure-change-value determining means for determining a change value of the blood pressure of the subject between a first time when the first blood pressure is measured by the first blood-pressure measuring device and a second time when the second blood pressure is measured by the second blood-pressure measuring device, based on a first piece of blood-pressure-relating information obtained by the blood-pressure-relating-information obtaining device at the first time and a second piece of blood-pressure-relating information obtained by the blood-pressure-relating-information obtaining device at the second time;

a corrected-blood-pressure determining means for determining, based on the change value determined by the blood-pressure-change-value determining means, one of the first and second blood pressures to a corrected blood pressure that would have been measured at one of the first and second times that corresponds to the other of the first and second blood pressures; and a blood-pressure-index determining means for determining the superior-and-inferior-limb blood-pressure index, based on the corrected blood pressure determined by the corrected-blood-pressure determining means and said other of the first and second blood pressures that has not been corrected by the corrected-blood-pressure determining means.

2. An apparatus according to claim 1, wherein the blood-pressure-relating-information obtaining device comprises a pulse-wave-propagation-velocity-relating-information obtaining device which iteratively obtains, as the piece of blood-pressure-relating information, a piece of pulse-wave-propagation-velocity-relating information relating to a velocity at which a pulse wave propagates through an artery of the subject.

3. An apparatus according to claim 1, wherein the first blood-pressure measuring device includes a right-ankle first inflatable cuff adapted to be wound around a right ankle of the subject, and a left-ankle first inflatable cuff adapted to be wound around a left ankle of the subject, and measures a right-ankle first blood pressure of the right ankle and a left-ankle first blood pressure of the left ankle, wherein the blood-pressure-change-value determining means determines a right-ankle first change value of the blood pressure of the subject between a right-ankle first time when the right-ankle first blood pressure is measured by the first blood-pressure measuring device and the second time when the second blood pressure is measured by the second blood-pressure measuring device, based on a right-ankle first piece of blood-pressure-relating information obtained by the blood-pressure-relating-information obtaining device at the right-ankle first time and the second piece of blood-pressure-relating information obtained by the blood-pressure-relating-information obtaining device at the second time, and additionally determines a left-ankle first change value of the blood pressure of the subject between a left-ankle first time when the left-ankle first blood pressure is measured by the first blood-pressure measuring device and the second time, based on a left-ankle first piece of blood-pressure-relating information obtained by the blood-pressure-relating-information obtaining device at the left-ankle first time and the second piece of blood-pressure-relating information obtained by the blood-pressure-relating-information obtaining device at the second time, wherein the corrected-blood-pressure determining means corrects, based on the right-ankle change value determined by the blood-pressure-change-value determining means, one of the right-ankle first blood pressure and the second blood pressure to a corrected blood pressure that would have been measured at one of the right-ankle first time and the second time that corresponds to the other of the right-ankle first blood pressure and the second blood pressure, and additionally corrects, based on the left-ankle change value determined by the blood-pressure-change-value determining means, one of the left-ankle first blood pressure and the second blood pressure to a corrected blood pressure that would have been measured at one of the left-ankle first time and the second time that corresponds to the other of the left-ankle first blood pressure and the second blood pressure, and wherein the blood-pressure-index determining means determines a right-side blood-pressure index, based on the corrected blood pressure determined by the corrected-blood-pressure determining means and said other of the right-ankle first blood pressure and the second blood pressure that has not been corrected by the corrected-blood-pressure determining means, and additionally determines a left-side blood-pressure index, based on the corrected blood pressure determined by the corrected-blood-pressure determining means and said other of the left-ankle first blood pressure and the second blood pressure that has not been corrected by the corrected-blood-pressure determining means.

4. An apparatus according to claim 1, further comprising a display device which displays at least one of the superior-and-inferior-limb blood-pressure index determined by the blood-pressure-index determining means and the piece of blood-pressure-relating information obtained by the blood-pressure-relating-information obtaining device.

5. An apparatus according to claim 1, wherein the blood-pressure-index determining means comprises means for determining, as the superior-and-inferior-limb blood-pressure index, at least one of a ratio of the first blood pressure to the second blood pressure, and a ratio of the second blood pressure to the first blood pressure.

6. An apparatus according to claim 1, wherein the blood-pressure-relating-information obtaining device comprises two pulse-wave sensors which are worn on two different portions of the subject, respectively, and each of which detects a pulse wave at a corresponding one of the two portions.

7. An apparatus according to claim 1, wherein the blood-pressure-change-value determining means comprises:

a relationship determining means for determining a relationship between estimated blood pressure and blood-pressure-relating information, based on at least one of the first and second blood pressures measured by the first and second blood-pressure measuring devices and at least one piece of blood-pressure-relating information obtained by the blood-pressure-relating-information obtaining device;

an estimated-blood-pressure determining means for determining, according to the determined relationship between estimated blood pressure and blood-pressure-relating information, a first estimated blood pressure of the subject based on the first piece of blood-pressure-relating information obtained by the blood-pressure-relating-information obtaining device at the first time, and a second estimated blood pressure of the subject based on the second piece of blood-pressure-relating information obtained by the blood-pressure-relating-information obtaining device at the second time, and determining the change value between the first and second estimated blood pressures of the subject.

8. An apparatus according to claim 1, further comprising:

a heart-contraction-relating-information obtaining device which iteratively obtains a piece of heart-contraction-relating information changing in relation with a change of a contraction period of a heart of the subject;

an abnormality judging means for judging, based on the pieces of heart-contraction-relating information iteratively obtained by the heart-contraction-relating-information obtaining device, whether each of the first and second pieces of blood-pressure-relating information obtained by the blood-pressure-relating-information obtaining device at the first and second times is abnormal; and a correct-blood-pressure-relating-information producing means for producing, when the abnormality judging means judges that said each of the first and second pieces of blood-pressure-relating information is abnormal, a correct piece of blood-pressure-relating information based on the iteratively obtained pieces of blood-pressure-relating information other than said each of the first and second pieces of blood-pressure-relating information judged as being abnormal, wherein the blood-pressure-change-value determining means determines, when the abnormality judging means judges that said each of the first and second pieces of blood-pressure-relating information is abnormal, the change value based on the correct piece of blood-pressure-relating information produced by the correct-blood-pressure-relating-information producing means.

* * * * *